United States Patent
Overeem et al.

(10) Patent No.: US 7,829,716 B2
(45) Date of Patent: Nov. 9, 2010

(54) PROCESS FOR MAKING MONTELUKAST AND INTERMEDIATES THEREFOR

(75) Inventors: Arjanne Overeem, Ede (NL); Reinerus G. Gieling, Nijmegen (NL); Jie Zhu, Nijmegen (NL); Lambertus Thijs, Wijchen (NL)

(73) Assignee: Synthon Pharmaceuticals, Inc., Research Triangle Park, NC (US)

( * ) Notice: Subject to any disclaimer, the term of this patent is extended or adjusted under 35 U.S.C. 154(b) by 911 days.

(21) Appl. No.: 11/081,689

(22) Filed: Mar. 17, 2005

(65) Prior Publication Data

US 2005/0245568 A1 Nov. 3, 2005

Related U.S. Application Data

(60) Provisional application No. 60/566,603, filed on Apr. 30, 2004, provisional application No. 60/584,675, filed on Jul. 2, 2004.

(51) Int. Cl.
*C07D 215/38* (2006.01)
*A61K 31/04* (2006.01)
(52) U.S. Cl. ...................... 546/174; 514/311
(58) Field of Classification Search ............... 546/174; 514/311
See application file for complete search history.

(56) References Cited

U.S. PATENT DOCUMENTS

| | | | |
|---|---|---|---|
| 5,266,568 | A | 11/1993 | Belley et al. |
| 5,270,324 | A | 12/1993 | Zamboni et al. |
| 5,523,477 | A | 6/1996 | King et al. |
| 5,565,473 | A | 10/1996 | Belley et al. |
| 5,585,115 | A | 12/1996 | Sherwood et al. |
| 5,614,632 | A | 3/1997 | Bhupathy et al. |
| 5,856,322 | A | 1/1999 | Belley et al. |
| 5,869,673 | A | 2/1999 | Tung et al. |
| 6,063,802 | A | 5/2000 | Winterborn |
| 6,320,052 | B1 | 11/2001 | Bhupathy et al. |
| 2004/0265375 | A1 | 12/2004 | Platteeuw et al. |
| 2005/0107426 | A1 | 5/2005 | Overeem et al. |
| 2005/0245569 | A1 | 11/2005 | Overeem et al. |

FOREIGN PATENT DOCUMENTS

| | | | |
|---|---|---|---|
| CN | 1420113 | * | 5/2003 |
| CN | 1428335 | * | 7/2003 |
| EP | 0 480 717 | | 4/1992 |
| WO | WO 95/18107 | | 7/1995 |

OTHER PUBLICATIONS

"An Efficient Synthesis of LTD₄ Antagonist L-699,392" by A.O. King et al., *J. Org. Chem.* 1993, 58, pp. 3731-3735.

* cited by examiner

*Primary Examiner*—D. Margaret Seaman
(74) *Attorney, Agent, or Firm*—Muncy, Geissler, Olds & Lowe, PLLC

(57) ABSTRACT

A process for making montelukast, a pharmaceutically useful compound of the following formula and salts thereof:

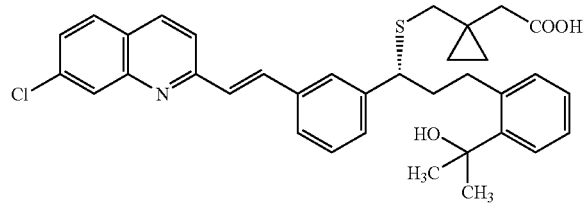

using a compound of formula (20)

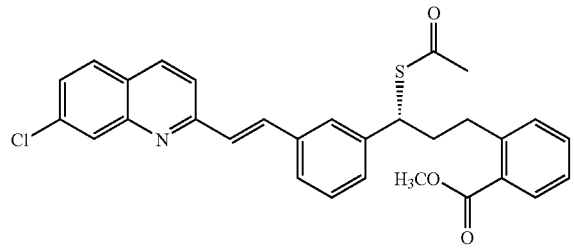

is provided.

19 Claims, No Drawings

PROCESS FOR MAKING MONTELUKAST AND INTERMEDIATES THEREFOR

This application claims the benefit of priority under 35 U.S.C. §119(e) from U.S. provisional application 60/566,603, filed Apr. 30, 2004, and from U.S. provisional application 60/584,675, filed Jul. 2, 2004, the entire contents of each provisional application being incorporated herein by reference.

BACKGROUND OF THE INVENTION

The present invention relates to a process for the synthesis of montelukast, a pharmaceutical agent, as well as to intermediates useful in the process.

Montelukast, chemically [R-(E)]-1-[[[1-[3-[2-(7-chloro-2-quinolinyl)ethenyl]phenyl]-3-[2-(1-hydroxy-1-methylethyl)phenyl]propyl]thio]methyl]cyclopropane acetic acid, has the following structure of formula (1):

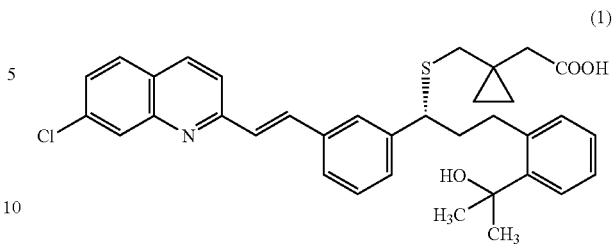

Montelukast monosodium salt (montelukast sodium) is commonly used for treatment of asthma. It is marketed under the brand name SINGULAIR® (Merck) in the form of oral tablets, chewable tablets, and granules.

U.S. Pat. No. 5,565,473 to BELLEY et al. (see also corresponding EP 0 480 717) discloses a genus of pharmaceutically useful compounds that encompasses montelukast and salts thereof. Example 161 in connection with example 146 of U.S. Pat. No. 5,565,473 disclose the synthesis of montelukast sodium as follows:

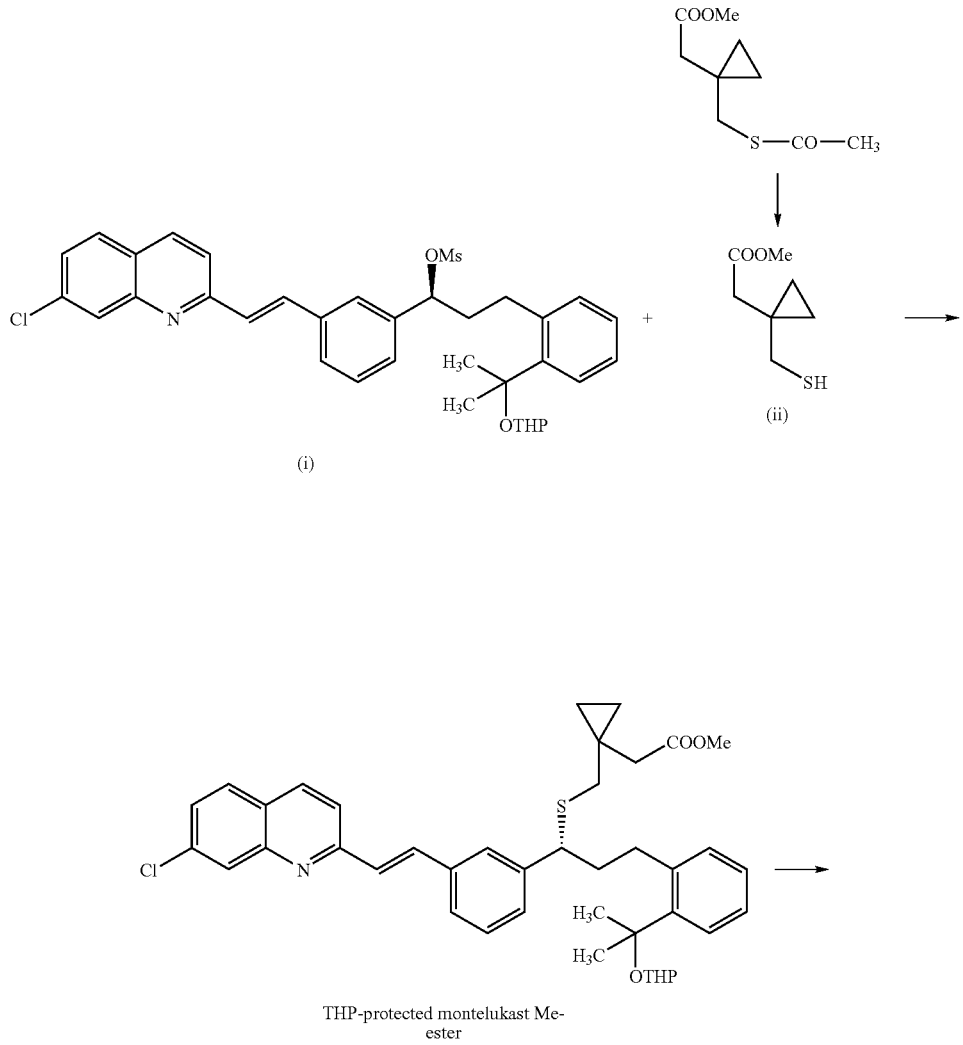

THP-protected montelukast Me-ester

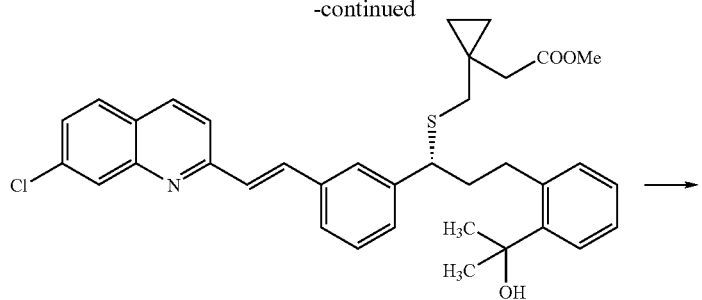

montelukast Me ester

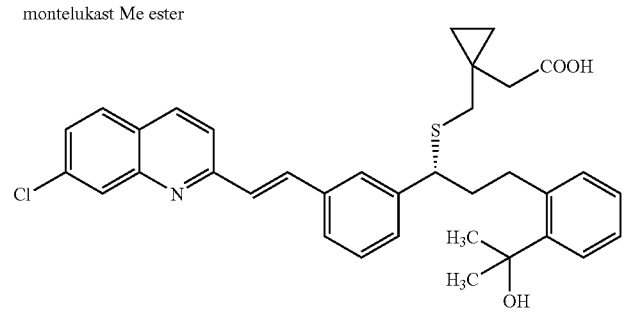

THP as used herein means tetrahydropyranyl group, typically of the formula:

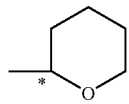

wherein the asterisk indicates a chiral carbon atom.

Many other synthetic schemes are proposed in U.S. Pat. No. 5,565,473 for making unsaturated hydroxyalkylquinoline acids, which may generically include montelukast. However, none of these other schemes were specifically applied to making montelukast. For example, Method B in U.S. Pat. No. 5,565,473 comprises reacting a compound of "general formula (XII)" with an organometallic compound of formula $R^2M$ to give a compound of "general formula (Ia)". Applying the corresponding substituent groups for montelukast, the method would follow the scheme below, wherein the compound of formula (2) is the representative compound of "general formula (XII)":

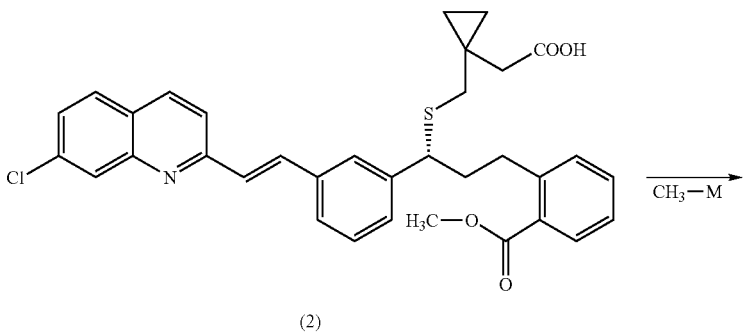

(2)

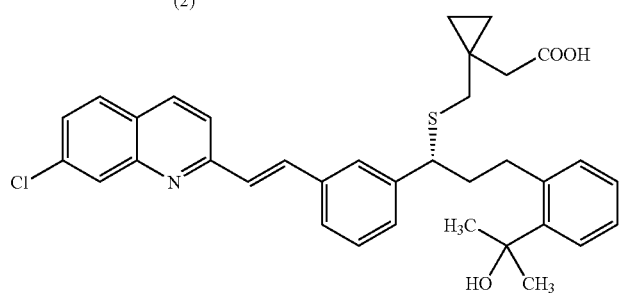

M is suggested to be MgBr or Li in Method A. The only disclosed process for making the compounds of "general formula (XII)" is not desirable for making montelukast, i.e. for making the hypothetical compound of formula (2). Specifically the process in Method B calls for a coupling reaction with a compound of "general formula (XI)." If applied to the corresponding substituents for montelukast, the reaction would be as follows:

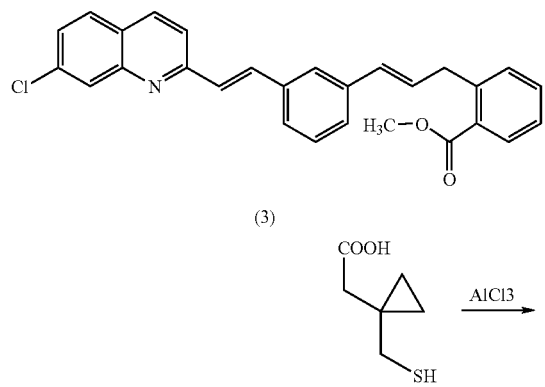

But this process cannot provide the compound (2) in the rigid R-configuration as suggested above, which is required for the montelukast synthesis. Instead, only a racemic product may be obtained and no method has been suggested how to resolve the racemate into single enantiomers.

Thus, there exists a need for providing a suitable process for making the compound of formula (2) and for providing conditions for its conversion to montelukast of formula (1).

SUMMARY OF THE INVENTION

The present invention is based on the discovery of a new process for making montelukast and the intermediates therefor. Accordingly, one aspect of the present invention relates to a compound of formula (20).

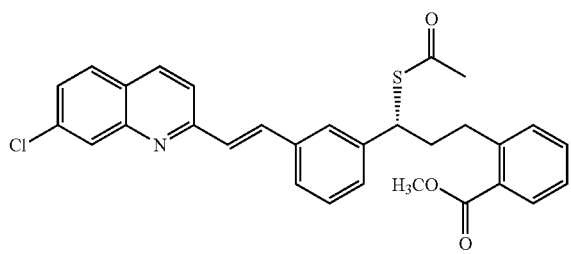

The compound of formula (20) is useful, inter alia, in the process for making montelukast.

Another aspect of the invention relates to a process which comprises reacting in the presence of a base a compound of formula (20):

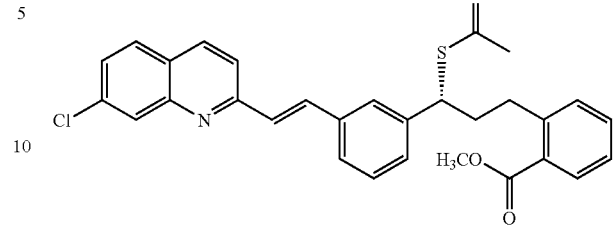

with a compound of formula (5):

wherein R is hydrogen or C1-C4 alkyl group, and L is a leaving group selected from a halogen or an alkyl- or arylsulfonyloxy group, to form a compound of formula (2) or (2a):

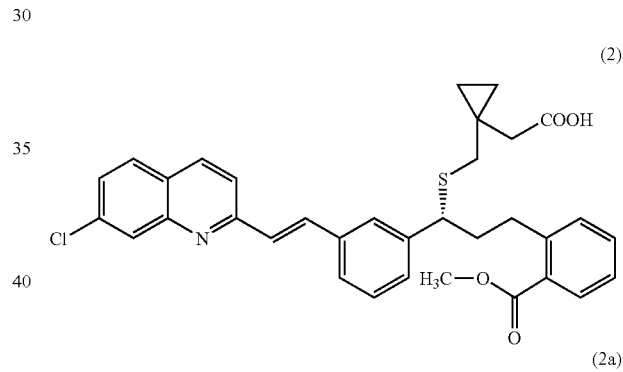

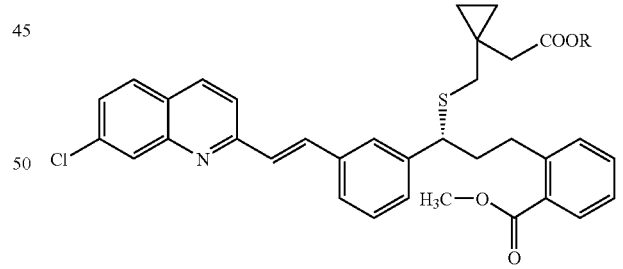

wherein R is a C1-C4 alkyl group. Thus, when R is hydrogen the compound (2) is directly formed. When R is a C1-C4 alkyl group, then the compound of formula (2a) is formed. Typically L represents a chloro, bromo, mesyloxy, besyloxy or tosyloxy group and the base is lithium hydroxide. The reaction can take place in an inert solvent and preferably under the atmosphere of an inert gas. The compounds of formula (2) and (2a) can be converted to montelukast or a salt thereof. The conversion generally comprises reacting the compound of formula (2) with a methyl lithium compound to form montelukast of formula (1). In this regard, if the compound of formula (2a) was formed, then it is usually hydrolyzed first to form the compound of formula (2) and then reacted with the methyl lithium compound.

Another aspect of the invention relates to a process for making montelukast, which comprises reactively contacting a compound of formula (2)

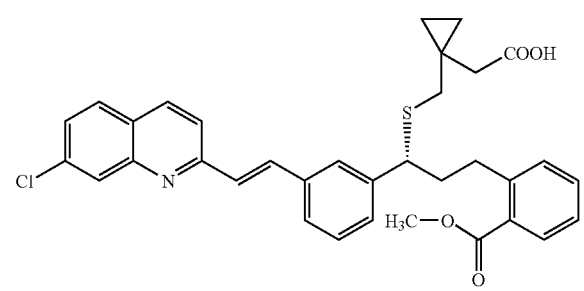

(2)

with a complex of methyl lithium and lithium bromide in an ether solvent to form montelukast of formula (1).

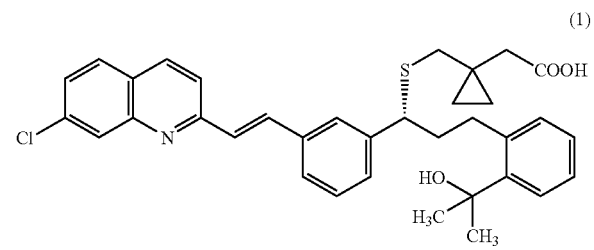

(1)

The ether solvent is typically tetrahydrofuran, diethyl ether or a combination thereof. The reaction temperature is generally from −40° C. to −10° C.

DESCRIPTION OF THE INVENTION

The present invention provides a new process for making montelukast and its salts, from a compound of formula (20). The suitable conversion of the compound of formula (20) into the desired key intermediate of formula (2) comprises the following sequence:

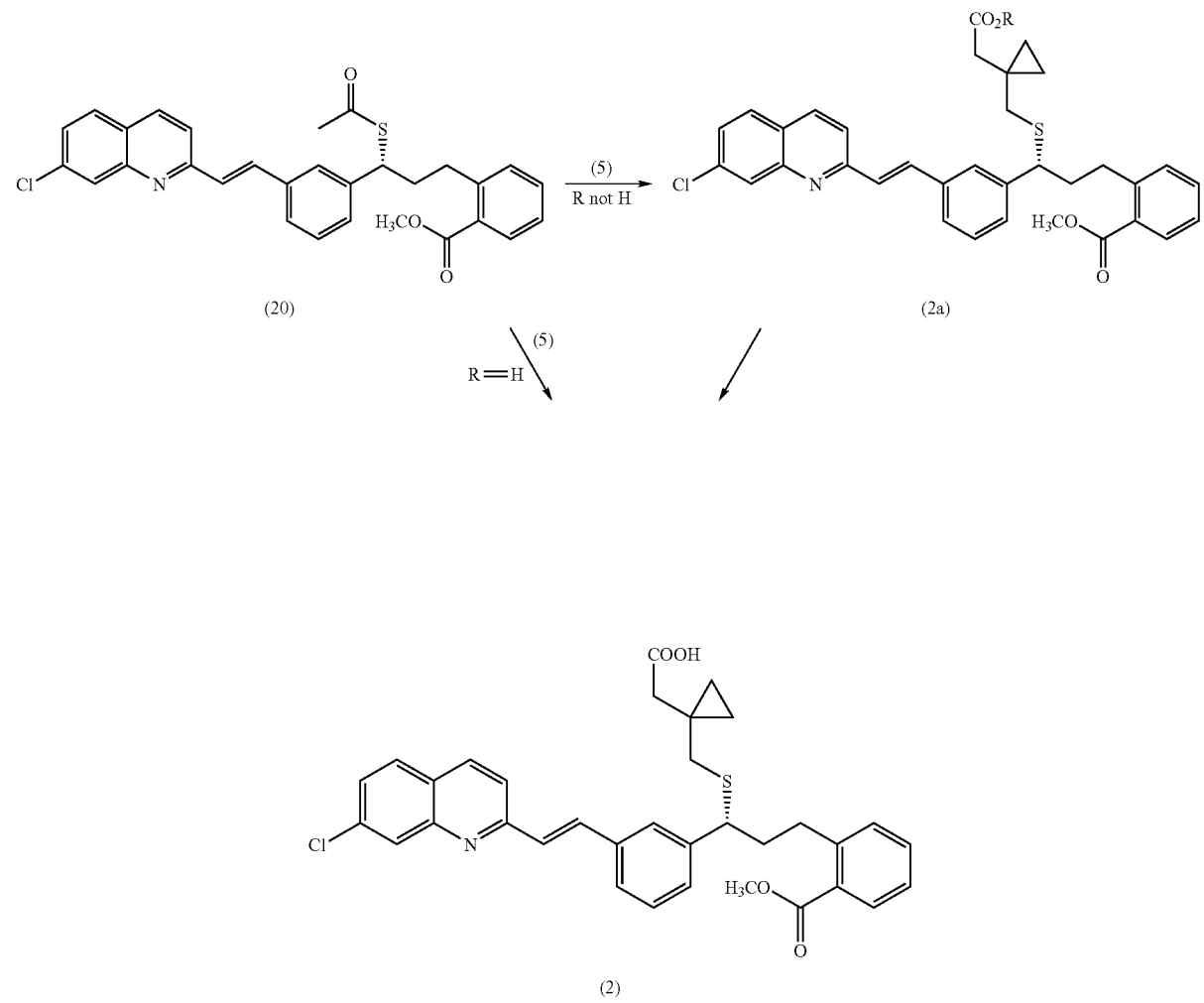

In the first step, the compound (20) is subjected to a reaction with a compound of formula (5). The R in the compound of formula (5) may be hydrogen or an C1-C4 alkyl group, but preferably is a methyl or ethyl group. The leaving group L may be halogen or and alkyl- or aryl-sulfonyloxy group, and typically is a bromo group.

The reaction of compound (20) with the compound (5) generally proceeds via a thiol intermediate (3).

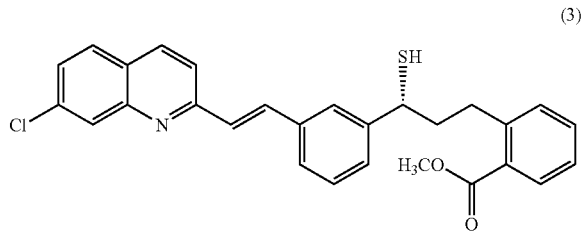

(3)

The thiol intermediate can be intentionally formed by a cleavage reaction using hydrazine or sodium methanolate, according to methods generally known in the art hydrazine contacting with the compounds (5). Such a two-step process is included within the scope of "reacting" the compound of formula (20) with a compound of formula (5). The thiol intermediate is very reactive and therefore it is also very sensitive to side reactions, particularly to the oxidation of the thiol group into a disulfide group. Thus under this embodiment of the reaction, the compound of formula (5) should be added shortly after the cleavage step in order to reduce impurities/side-products; generally within three hours and typically within one hour. But more preferably the separate step of cleaving, i.e. prior to adding the compound (5) into the reaction mixture, is avoided. Instead, the reaction can be directed in such a way that the thiol group is formed, if at all, in situ as part of the reaction mechanism and in the presence of the compound (5). In this way, the thiol intermediate can react immediately after its formation. This can be achieved, for instance, by the use of lithium hydroxide. The lithium hydroxide both cleaves the S—COCH₃ bond and serves as a base for the nucleophilic substitution of the side chain (5) as well. This kind of reaction allows for the efficient conversion of the compound of formula (20) to a compound of formula (2) or (2a) in a one pot process and/or one step process. Of course, the compound of formula (5) could be added subsequently, i.e. after cleaving begins or has completed via the lithium hydroxide, in an analogous manner as the first reaction scheme embodiment, though such a method is generally not advantageous. The reaction normally proceeds in a solvent, which is preferably a mixed solvent containing an alcohol, for instance a methanol/acetonitrile mixture for the one pot process embodiment just described. The reaction is typically carried out under an atmosphere of an inert gas, such as nitrogen or argon. The combination of the above conditions serves to minimize the undesired side reaction of the thiol group into a disulfide group.

When the product of the reaction is an ester compound of formula (2a), it is normally converted by hydrolysis to provide the compound (2). Preferred hydrolytic conditions comprise an alkaline hydrolysis. Care is to be taken during the alkaline hydrolysis, as the second ester group (at the benzoate moiety) may also be hydrolyzed resulting in the formation of an undesired diacid. The diacid, if formed, may however be removed from the desired acid (2) by washing the reaction mixture with a diluted sodium carbonate solution, in which the diacid, contrary to of the acid (2), is far more soluble and may be thus removed.

The compound of formula (2), either formed directly or after hydrolysis of the compound of formula (2a), can be converted into montelukast by any suitable means as suggested by the prior art. However, a preferred method of the present invention uses a methyl lithium compound. As methyl lithium itself is unstable, there exist various commercial products comprising methyl lithium, e.g. solutions of methyl lithium in various solvents, preferably in an ether solvent. It has been discovered that when the "methyl lithium compound" is a complex of methyl lithium with lithium bromide, good results can be obtained. Such a complex is also available commercially in an ether solution. Consequently, it is convenient, but not required, that the reaction of the compound (2) with the methyl lithium compound proceeds in an ether solvent. Typical ether solvents include tetrahydrofuran, diethyl ether and combinations thereof. The reaction generally proceeds under temperatures below 0° C., preferably between −10 and −40° C. A 2-4 fold molar equivalent of methyl lithium is usually required. The completion of reaction may be monitored by suitable method, for instance by HPLC. After completing the reaction, the remainder of the methyl lithium compound is decomposed by conventional methods, for instance by ammonium chloride, the inorganic side products are removed by extraction with water, and the product is isolated by any suitable method.

The product of the reaction is montelukast acid. It may be used in pharmaceutical applications per se, for instance in a solid form, which has been disclosed in U.S. patent application Ser. No. 10/960,639, filed Oct. 8, 2004, entitled "Solid State Montelukast," the entire contents of which are incorporated herein by reference. Alternately, the montelukast acid may be converted into various salts, of which the sodium salt is preferred.

A suitable process for making the starting compound of formula (20) starts from a methyl ester compound (18) as shown in the following reaction scheme:

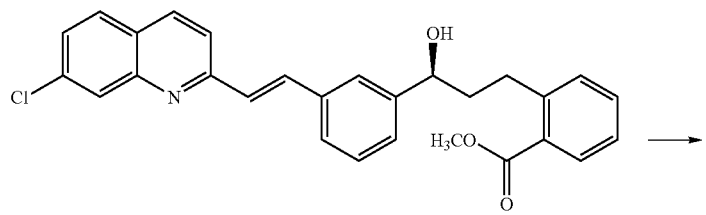

18

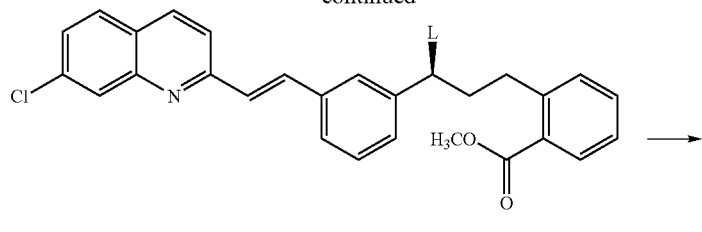

19

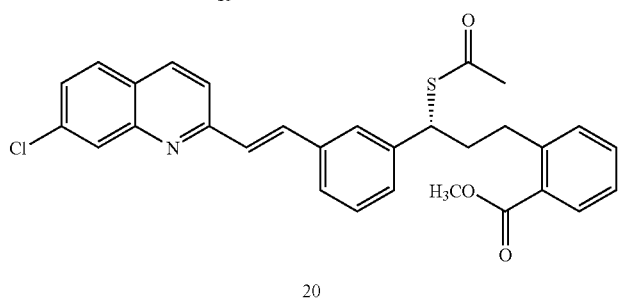

20

The compound (18) is also a known compound of the prior art (see Compound XXVII in EP 480717) and can be produced by Steps 1-2 of the example 146 in EP 480717. It can be isolated in solid form as a monohydrate.

A suitable process for conversion of the compound (18) into compound (20) comprises the following sequence:

In the first step, the OH— group in (18) is first made labile by converting it into a reactive group L such as an alkyl- or aryl sulfonyloxy group, preferably a mesyloxy group. The product is the compound of general formula (19). Preferred is the compound bearing the mesyloxy group (19a).

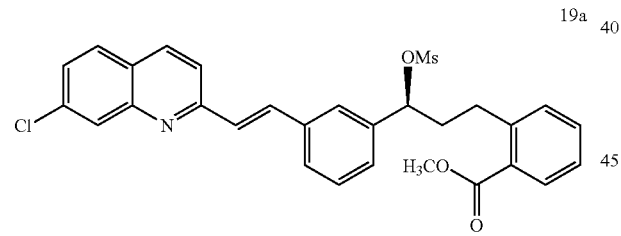

19a

The mesylation reaction comprises contacting compound (18) with methanesulfonyl chloride in an inert solvent in the presence of a suitable base, e.g. a tertiary amine such as triethylamine.

The labile compound (19) is then converted into acetylthio ester compound (20) by reaction with a thioacetic acid or salt thereof, preferably sodium or potassium thioacetate, in an inert solvent. In this way, the labile L- group is replaced by the CH₃—CO—S— group. The reaction normally proceeds in a suitable inert solvent such as toluene, dimethylformamide or mixtures thereof, and generally at temperatures close to and including ambient, e.g. 0-40° C.

The process of making the starting compounds of formula (5) wherein R represents a C1-C4 alkyl, specifically methyl, was suggested in Example 161 of U.S. Pat. No. 5,565,473. The process starts with diethyl 1,1-cyclopropanedicarboxylate and comprises the following reaction sequence:

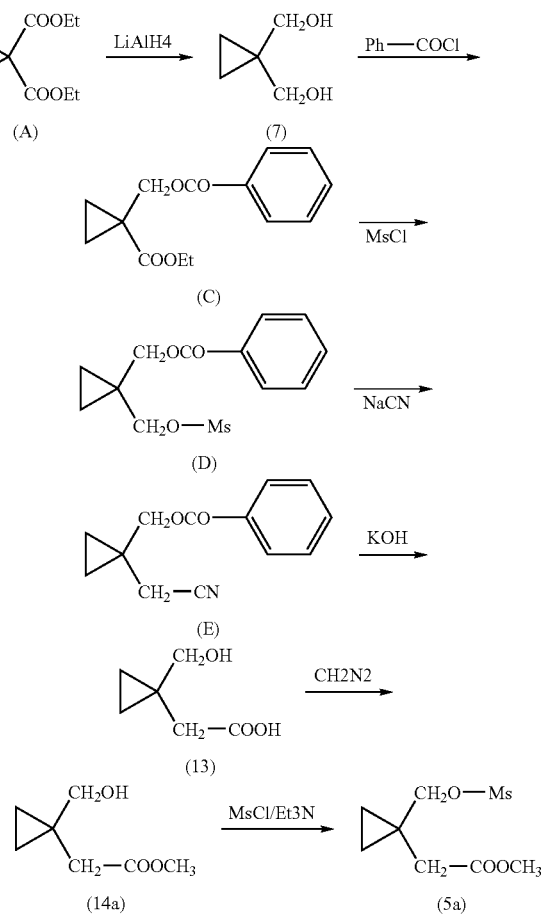

While such a reaction scheme can be used to obtain a compound of formula (5a), it is not advantageous. The main problem in obtaining the compound (5a) and, in analogy, any compound of the general formula (5), by this method is the low overall yield caused by the impossibility of obtaining selective monobenzoyl protection of the diol (B). The disclosed process (step 2 of Example 161), provides only a mixture of mono- and di-benzoylated diol in approximately equal yield. Apart from the fact that approx. 50% of the starting material is thereby lost, the resulting mixture of diols has to be resolved by two-fold column chromatography, which is inconvenient for scaling up.

The compound (5) may also be produced by two novel reaction sequences starting from the compound (7).

One reaction scheme is set forth below:

This first scheme for making the starting ester compound of formula (5) relates to the surprising discovery that 1,1-cyclopropane dimethanol (7) may react with a benzaldehyde compound (8), wherein X is hydrogen, hydroxy, methoxy, halo, methyl, trifluoromethyl or nitro group, preferably the methoxy group, under conditions susceptible to form an acetal, whereby the OH-protection in the form of an acetal has the substantial advantage that selective deprotection can be done stepwise. That is, in a first deprotection step only one OH— group is liberated and subjected to further reactions, while the remaining one remains protected for the desired

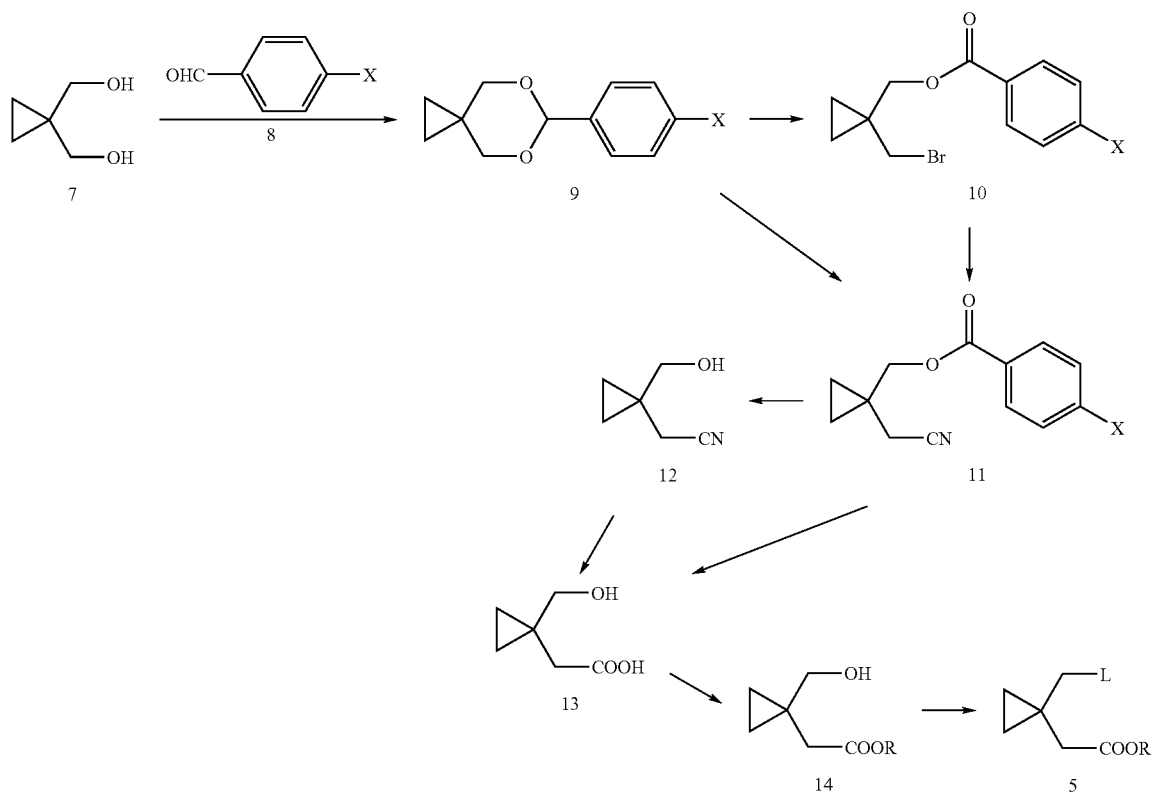

The scheme comprises
a) protection of both OH— groups in 1,1-cyclopropane dimethanol (7) by a benzaldehyde compound (8) to yield a cyclic acetal compound (9);
b) oxidative opening of (9) under formation of mono-benzoyl nitrile compound (11), preferably via a monobenzoyl bromo compound (10);
c) deprotection of the OH— group and hydrolysis of the cyano group in (11) to yield the hydroxymethyl carboxylic acid compound (13), preferably via the hydroxymethyl nitrile compound (12);
d) esterification of the acid (13) with an C1-C4 alcohol in a presence of an acid to yield an ester compound (14); and
e) conversion of the ester (14) into the labile ester compound (5).

X is hydrogen, hydroxy, methoxy, chloro, bromo, fluoro, methyl, trifluoromethyl or nitro group; L is a leaving group typically a halogen or an alkyl- or aryl-sulfonyloxy group such as chloro, bromo, mesyloxy, besyloxy or tosyloxy group; and R is a C1-C4 alkyl group. Preferably, X=methoxy, L=bromo or mesyloxy and R is ethyl group.

time and is liberated only at the moment of need. Thus the formation and use of the compound of formula (9) is a particular aspect of the invention, especially in forming the compound (5).

A useful benzaldehyde compound (8) for the above protection is p-anisaldehyde (8a) (compound 8, X=methoxy)

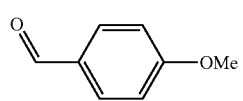

which has the advantage that the resulting acetal (9a)

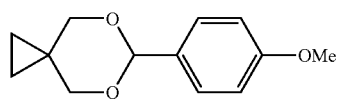

may be isolated as a solid material and may be purified from the excess of reagents and side contaminants.

The reaction between (7) and (8), preferably (8a), normally proceeds in a suitable non polar solvent such as benzene, toluene, hexane or cyclohexane at temperatures up to reflux and is either catalyzed by an acid, particularly by p-toluenesulfonic acid, or proceeds under neutral conditions catalyzed by, e.g., pyridinium p-toluene sulfonate (PPTS). The water formed by the reaction is advantageously removed, e.g. by azeotropic distillation, by a molecular sieve or by any other conventional process.

The next step comprises the oxidative opening of the acetal (9) under formation of the protected nitrile (11). Suitable oxidant is DDQ or p-chloranil; water present in the reaction mixture should be avoided. In the presence of water, partial or complete deprotection may be obtained yielding the undesired alcohol or diol. From practical reasons, the reaction may be performed stepwise. In the first step, the oxidative opening of the acetal ring in an anhydrous environment is performed in the presence of a bromide donor having a character of Lewis acid to produce the protected bromo compound (10). Suitable bromide donors, optionally in combination with a Lewis acid, include $CuBr_2$, LiBr, and a combination of $Bu_4NBr/CuBr_2$. About one molar equivalent of DDQ is sufficient, as higher amounts generally do not increase the speed and yield of the reaction. Suitable solvent for the reaction is an aprotic solvent, e.g. 1,2-dichloroethane, toluene or dichloromethane; the reaction readily proceeds even at ambient temperature but may be speeded up by heating the mixture up to the boiling point; however higher temperatures often cause the formation of impurities.

The monobenzoyl bromo derivative (10) may be advantageously purified from side products (particularly from monobenzoyl alcohol) by conventional means, e.g. by chromatography on silica gel, but can be used in the next step in a crude state as well.

Reaction of the monobenzoyl bromo derivative (10) with metal cyanide, e.g. sodium or potassium cyanide yields the protected nitrile compound (11). The reaction proceeds in a suitable solvent, e.g. ethanol/water mixture.

If a cyanide donor is used instead of the bromide donor in the oxidative opening of compound (9), the reaction may directly lead to the protected nitrile (11), without forming and isolating the protected bromide.

Upon treatment of the protected nitrile (11) with a base, e.g. with sodium or potassium hydroxide, the benzoyl group may be removed and a deprotected nitrile (12) is formed. Simultaneously, the cyano group in (12) is susceptible to a hydrolysis by the base. The final product of deprotection and hydrolysis is, after neutralization of the alkaline environment and removal of inorganic side products, the hydroxymethyl carboxylic acid (13). For practical reasons, the reactions may be advantageously performed stepwise in as much as the split-off benzoic acid can be better removed from the product in the stage of the nitrile compound (12). For instance, the nitrile can be extracted well from the alkaline reaction medium by a non-polar solvent. Thus, it is generally preferred to use mild conditions for the treatment with a base, under which only the deprotection occurs (a temperature close to ambient), to purify the obtained deprotected nitrile (12) from the liberated side product comprising the original protective group, and then to carry out the hydrolysis of the nitrile group. The nitrile hydrolysis may be performed, e.g., by heating the nitrile with an alkali metal hydroxide in water, lower alcohol or in a mixture of both. After neutralization of the alkaline environment used for the hydrolysis, the acid (13) is obtained. It may be isolated as a solid product and/or purified by conventional means, for instance by crystallization from a suitable solvent, for instance from ethyl acetate. Solid crystalline form of the acid (13) is another aspect of the present invention.

In the next step, the acid (13) is esterified. For methyl esters, this can be carried out as shown in Example 161 of U.S. Pat. No. 5,565,473 (see also compound (f) in the Example 161 reaction scheme shown above) by treatment of the acid compound with diazomethane to yield the methyl ester (14a) (compound 14, R=$CH_3$). But, diazomethane is a toxic and explosive compound and can only form the methyl ester. Surprisingly, it has been discovered that the hydroxymethyl acid (13), which is expected to be sensitive to acidic environment/conditions, can be esterified by conventional techniques including by treatment with a corresponding alcohol under catalysis of a strong acid. This allows for a more safe and convenient way for an industrial process and, moreover, it allows to produce a variety of esters of formula (14), not only the methyl ester (14a). The preferred ester is the methyl ester (14a) or ethyl ester (14b) formed by using methanol and ethanol, respectively.

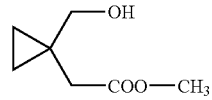

Furthermore, no column chromatography is required within the above process.

In the last step, the ester (14), for instance the methyl ester (14a) or ethyl ester (14b), is converted into the labile ester (5) (R=C1-C4 alkyl) by methods known per se. The labile group L preferably comprises bromo- or mesyloxy group. Preferred compounds of formula (5) are compounds (5a) to (5d).

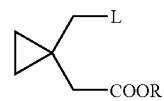

5a: L = O-Ms and R = $CH_3$
5b: L = O-Ms and R = $C_2H_5$
5c: L = Br and R = $CH_3$
5d: L = Br and R = $C_2H_5$ For instance, the compounds (5a) and (5b) may be made by reacting the corresponding ester of formula (14) with a mesylchloride.

A second improved process for making the ester compounds of formula (5) involves converting the starting compound of formula (7) into a compound of formula (12) by a route that can be represented by the following scheme:

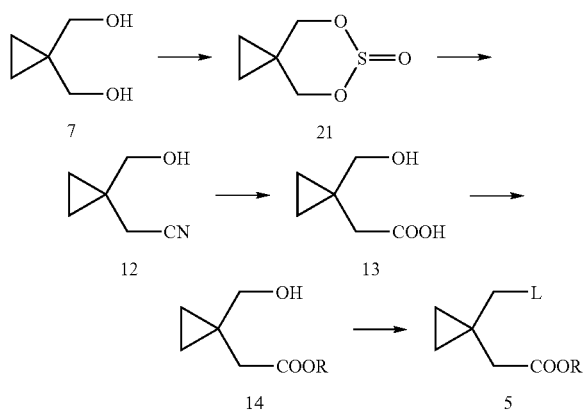

The scheme comprises:
a) reacting 1,1-cyclopropane dimethanol (7) with thionyl chloride or with a dialkyl sulfite, wherein each alkyl group is a C1-C4 alkyl, to yield a compound of formula (21);
b) reacting the compound (21) with an alkali metal cyanide to form a compound (12);
c) hydrolyzing the cyano group in the compound (12) to form a hydroxymethyl carboxylic acid compound (13);
d) esterification of the acid (13) with an C1-C4 alcohol in a presence of an acid to yield an ester compound (14); and
e) conversion of the ester (14) into the labile ester compound (5).

In the first step, the compound (7) reacts with thionyl chloride or with a dialkyl sulfite, preferably dimethyl sulfite or di-isopropylsulfite to yield a cyclic sulfite compound (21). The alkyl groups are generally the same, although different alkyls are not excluded. The compound (21) is generally isolated as a solid product and, if desired, purified from side products. Whether isolated or not, the compound of formula (21) is then reacted with an alkaline metal cyanide, preferably with sodium cyanide, to form the compound of formula (12). Both of these steps (a) and (b) can be performed using the conditions described in U.S. Pat. No. 5,270,324 or U.S. Pat. No. 5,523,477 for the thionyl chloride-based or the dialkyl sulfite-based variant, respectively. The obtained nitrile of formula (12), typically in an isolated form, is then transformed into the compound (5) as described above for the first general process.

The invention is further described by way of the following non-limiting examples.

Example 1

Methyl 2-[1-(hydroxymethyl)cyclopropyl]acetate (14a)

5 g 2-[1-(hydroxymethyl)cyclopropyl]acetic acid (compound (13)) was dissolved in 65 ml methanol and 80 mg sulfuric acid was added. The reaction mixture was stirred overnight at room temperature; reaction progress was monitored by GC. The pH of the reaction mixture was adjusted to 7 with saturated NaHCO$_3$. The reaction mixture was evaporated to dryness. 75 ml of ethyl acetate and 10 ml brine were added. The water layer was washed with 20 ml ethyl acetate. The combined organic layers were dried (Na$_2$SO$_4$) and evaporated to dryness, resulting in a yellow oil.

Isolated yield: 5.44 g $^1$H-NMR: confirmed the structure

Example 2

Methyl 2-[1-(bromomethyl)cyclopropyl]acetate (compound 5c)

Step 1: Methyl 2-(1-1 [(methylsulfonyl)oxy]methylcyclopropyl)acetate (compound 5a)

8.45 g of crude methyl 2-[1-(hydroxymethyl)cyclopropyl] acetate (compound 14a) was dissolved in 85 ml dry dichloromethane. The pale yellow solution was cooled to 0° C. Then, 7.71 g triethylamine was added and 8.05 g methanesulfonyl chloride was added dropwise over 8 minutes. The yellow suspension was stirred at 0° C. TLC showed that after 10 minutes the reaction was completed. To the reaction mixture, 35 ml water and 20 ml dichloromethane were added. The water layer was washed with 20 ml dichloromethane. The combined organic layers were washed with 30 ml water, dried (Na$_2$SO$_4$) and evaporated to dryness, resulting in a yellow oil. The product was immediately used in the next step (synthesis of methyl 1-(bromomethyl)-cyclopropaneacetate).

Isolated yield: 13.24 g

Step 2: Methyl 2-[1-(bromomethyl)cyclopropyl]acetate (compound 5c)

13.24 g of crude (5a) was dissolved in 140 ml dry tetrahydrofuran. 7.7 g lithium bromide was added. The white suspension was stirred at room temperature overnight; reaction progress was monitored by GC. The reaction mixture was concentrated in vacuo to about 40 ml and 120 ml dichloromethane and 30 ml water were added. The organic layer was washed with 30 ml sat. NaHCO$_3$ and 30 ml brine, dried (Na$_2$SO$_4$) and evaporated to dryness, resulting in a yellow oil.

Isolated yield: 12.13 g $^1$H-NMR: confirmed the expected structure

Example 3

Ethyl 2-(1-{[(methylsulfonyl)oxy]methylcyclopropyl)acetate (compound 5b)

Step 1: 1,1-cyclopropanedimethanol O-p-methoxybenzylidene acetal (compound 9a)

3.63 g 1,1-cyclopropanedimethanol (compound (7) was dissolved in 50 ml of cyclohexane. 4.85 g p-anisaldehyde and 250 mg p-toluenesulfonic acid were added. The mixture was heated to reflux and water was distilled off azeotropically. After two hours, the mixture was allowed to cool to room temperature and left overnight. Cyclohexane was removed at reduced pressure, affording a yellow oil. The crude product was dissolved in ethyl acetate and washed with saturated bicarbonate solution and brine, dried with sodium sulfate and concentrated. The resulting crude product mixture was crystallized from ethanol, affording 700 mg 1,1-cyclopropanedimethanol O-p-methoxybenzylidene acetal as slightly yellow crystals.

Step 2: 1-(p-methoxybenzoyloxy)methyl 1-bromomethyl cyclopropane (compound 10a)

1 mmol of the acetal from the Step 1 was dissolved in 5 ml of 1,2-dichloroethane (distilled with calcium chloride, stored on molecular sieves) under nitrogen atmosphere. 1 mmol copper(II)bromide and 1 mmol tetrabutyl ammonium bromide were added and the mixture was stirred for 30 min. at room temperature. The oxidizing agent (DDQ or chloranil; 1-2 mmole) is added and the mixture is stirred until the starting material has disappeared on TLC. Ethyl acetate is added to the reaction mixture at room temperature and washed twice with a saturated aqueous bicarbonate solution. After concentration of the organic phase, the crude product is obtained.

For analytical purposes, the crude product is dissolved in heptane/ethyl acetate: 4/1 and eluted over silica. The filtrate is dried ($Na_2SO_4$) and evaporated to give the title product.

Step 3—the 1-(p-methoxybenzoyloxymethyl)cyclopropane-1-acetonitrile (11a)

261 mg of compound 10a was dissolved in 5 ml ethanol. A solution of 98 mg potassium cyanide in 5 ml water was added and the mixture was stirred at 35° C. for two days. 10 ml of a saturated aqueous sodium bicarbonate was added. The mixture was extracted twice with ethyl acetate. The combined extracts were dried with sodium sulfate and evaporated to give a yellow liquid. Purification with column chromatography (heptane/ethyl acetate 3/1) gave the title compound (38 mg) confirmed by NMR and LC/MS.

Step 4—1-(hydroxymethyl)-cyclopropane-1-acetonitrile (12)

0.16 mol of the compound (11a) was dissolved in 250 ml of ethanol and 250 ml of 4M aqueous potassium hydroxide was added. The mixture was stirred for 90 minutes at room temperature. Ethanol was evaporated and the remaining aqueous solution was extracted twice with 250 ml of dichloromethane. The combined organic layers were washed twice with 250 ml of aqueous sodium bicarbonate and one with 250 ml of brine. Drying the organic layer over anhydrous sodium sulfate and evaporating gave the title compound as an orange liquid (16.2 g).

Step 5: 1-(hydroxymethyl)cyclopropyl acetic acid (13)

15.6 g of the compound (12) was dissolved in 100 ml of ethanol. 150 ml of 8M aqueous potassium hydroxide was added and the mixture was stirred at reflux for 17 hours. Ethanol was evaporated and the remaining aqueous solution was cooled to 2° C. Concentrated hydrochloric acid was added dropwise at a temperature of 4-6° C. When the pH decreased to below 1, the aqueous mixture was decanted from the white precipitate and extracted four times with 125 ml of ethyl acetate. The solid was thoroughly washed with ethyl acetate. The combined ethyl acetate layers were dried over anhydrous sodium sulfate and evaporated to give title compound as a crude product (8.9 g).

For analytical purposes, the crude product was crystallized from ethyl acetate (1.2 g of crystals were obtained). The mother liquor was evaporated and the recovered crude product was used in the esterification reaction (7.4 g).

Step 6: Ethyl 2-[1-(hydroxymethyl)cyclopropyl]acetate (14b)

7.1 g of crude (13) product was dissolved in 150 ml of ethanol. 1 ml of concentrated sulfuric acid was added and the solution was stirred at reflux for 2 hours. 50 ml of saturated aqueous sodium bicarbonate was added to the cooled mixture and the mixture was extracted twice with 100 ml of dichloromethane. The combined organic extracts were dried over anhydrous sodium sulfate and evaporated. The crude product was distilled at 100° C. at a reduced pressure affording a slightly yellow liquid (3.2 g).

Step 7: Ethyl 2-(1-[(methylsulfonyl)oxy]methylcyclopropyl)acetate (5b)

253 mg of compound 14b and 225 µl triethylamine were dissolved in 10 ml dichloromethane and cooled to −50° C. 140 µl methanesulfonylchloride was added and the mixture was stirred for one hour allowing the temperature to increase to 0° C. Saturated aqueous sodium bicarbonate was added and the mixture was extracted twice with dichloromethane. The organic extracts were combined and dried with sodium sulfate. Evaporation of the solvent gave 308 mg of the title compound as an almost colorless liquid.

Structure confirmed by NMR.

Example 4

Ethyl 2-[1-(hydroxymethyl)-cyclopropyl]acetate (compound 14b)

6.0 g 2-[1-(hydroxymethyl)cyclopropyl]acetic acid (compound (13) was dissolved in 120 ml ethanol followed by addition of 6 drops of conc. sulfuric acid. The mixture was stirred at room temperature overnight. The mixture was concentrated partly to remove ~40 ml ethanol and further stirred at room temperature ("rt") for another day. The mixture was neutralized to pH~7 (using ~3 ml aq. saturated $NaHCO_3$) and concentrated in vacuo. After re-dissolving in ethylacetate (200 ml), it was washed with brine (15 ml), dried and concentrated in vacuo to give a light-yellow oil (6.85 g).

Example 5

Methyl 2-((3R)-acetylsulfanyl)-3-[3-[(E)-2-(7-chloro-2-quinolinyl)-ethenyl]-phenyl]-propyl)-benzoate (compound (20))

Step 1:

Methyl 2-((3S)-3-[2-(7-chloro-2-quinolinyl)-ethenyl]-phenyl)-3-methanesulfonyloxy-propyl)benzoate (compound (19))

3 g of Methyl 2-((3S)-3-[2-(7-chloro-2-quinolinyl)-ethenyl]-phenyl)-3-hydroxypropyl)benzoate monohydrate [Compound (18)] was slurried in 100 ml of toluene and was azeotropically dried under reduced pressure. The resulting brown oil was dissolved in 75 ml of dry dichloromethane. The solution was cooled to −40° C. Then 938 mg methanesulfonyl chloride and 957 mg triethylamine were added. The orange/brown solution was stirred at −40° C. for 30 minutes and at 0° C. for 1 hour. The reaction mixture was washed with 2×75 ml water. The organic layer was dried (Na$_2$SO$_4$), filtered, and evaporated to dryness resulting in an orange/brown oil.

Step 2: Compound (20)

The oil was dissolved in 36 ml toluene and 12 ml DMF and then 849 mg of potassium thioacetate was added and the reaction mixture was stirred over night at room temperature. TLC showed a slight amount of starting material. 75 ml of ethyl acetate and 75 ml water were added. The water layer was washed with 20 ml ethyl acetate. The combined organic layers were washed with 2×75 ml water, dried (Na$_2$SO$_4$), filtered and evaporated to dryness, resulting in 3.85 g of a brown oil. The crude product was purified by column chromatography using Silica (20-45 micron) and heptane/ethyl acetate (85/15→80/20) as eluens. Pure fractions were collected and evaporated to dryness, resulting in a yellow oil.

Isolated yield: 1.87 g (57%)

$^1$H- and $^{13}$C-NMR confirmed the expected structure

Example 6

Methyl 2-((3R)-acetylsulfanyl)-3-{3-[(E)-2-(7-chloro-2-quinolinyl)-ethenyl]-phenyl}-propyl)-benzoate (Compound (20))

Step 1: Synthesis of Compound (19)

5 g of the compound (18) (monohydrate) was slurried in 120 ml of toluene and was azeotropically dried under reduced pressure. The resulting brown oil was dissolved in 80 ml of dry toluene. The solution was cooled to −40° C. 1.56 g methanesulfonyl chloride and 1.59 g triethylamine were added. The reaction mixture was stirred at −40° C. for 45 minutes and then at 0° C. for 45 minutes. The reaction mixture was washed with 2×100 ml brine. The organic layer was dried (Na$_2$SO$_4$), filtered, and evaporated to dryness, resulting in an orange/brown oil.

Step 2: Synthesis of Compound (20)

The oil was dissolved in 60 ml of toluene and 20 ml of dimethylformamide. Then 1.42 g potassium thioacetate was added and the reaction mixture was stirred over night at room temperature. TLC showed still a slight amount of starting material. The reaction mixture was stirred for 24 hrs at RT. TLC showed still a slight amount of starting material. 80 ml of ethyl acetate and 80 ml of water were added. The water layer was washed with 20 ml ethyl acetate. The combined organic layers were washed with 2×80 ml water, dried (Na$_2$SO$_4$), filtered, and evaporated to dryness, resulting in 6.1 g of a brown oil. The crude product was purified by column chromatography using Silica (20-45 micron) and heptane/ethyl acetate (85/15→80/20) as eluens. Pure fractions were collected and evaporated to dryness, resulting in a yellow oil.

Isolated yield: 3.69 g (68%)

$^1$H-NMR: confirmed the expected structure

Example 7

Methyl 2-((3R)-acetylsulfanyl)-3-{3-[(E)-2-(7-chloro-2-quinolinyl)-ethenyl]-phenyl}-propyl)-benzoate (compound 20)

23.8 g of the compound (18) (monohydrate) was slurried in 600 ml toluene and azeotropically dried to result in ~450 ml of toluene solution. The obtained solution was cooled to −30° C. 7.60 g triethylamine was added followed by the addition of 7.48 g methanesulfonyl chloride over 3 minutes. The reaction mixture was allowed to slowly warm to 0° C. over 1.5 hours. 100 ml water was added and the mixture was stirred for 20 minutes. The organic layer was washed with 100 ml brine, dried (Na$_2$SO$_4$) and filtered. An additional 50 ml toluene was used for washing, so to in total about 500 ml toluene solution was obtained. To this solution, 160 ml DMF and 6.84 g potassium thioacetate were added. The reaction mixture was stirred mechanically for 3.5 hrs at 40-42° C. Reaction progress was monitored with HPLC. The reaction mixture was cooled to room temperature. 600 ml water was added. After stirring for 15 minutes, the organic layer was washed twice with 120 ml brine, dried (Na$_2$SO$_4$) and evaporated to dryness, resulting in an orange/brown oil.

Isolated yield: 28.5 g $^1$H-NMR: confirmed the expected structure

Example 8

Synthesis of Montelukast

Step 1: Methyl 2-{(3R)-3-[3-[(E)-2-(7-chloro-2-quinolinyl)ethenyl]-phenyl]-5-[1-(2-methoxy-2-oxo-ethyl)cyclopropyl]pentyl}benzoate (2a)

26.9 g of compound (20) was dissolved in a mixture of 175 ml acetonitrile and 350 ml methanol. 12.5 g methyl 2-[1-(bromomethyl)cyclopropyl]acetate (compound 5c) was added. The reaction mixture was stirred at room temperature, while nitrogen was bubbled through the mixture for 2 hours. A solution of 2.15 g lithium hydroxide monohydrate in 11 ml water was added dropwise over 10 minutes to the dark brown solution. The reaction mixture was stirred at room temperature; reaction progress was monitored with HPLC. After 2 hours 20 minutes, a second addition of 150 mg lithium hydroxide monohydrate in 1 ml water was made. After 3 hours, stirring was stopped. The solution (brown, clear) was decanted. The remaining dark brown oil was washed with 7 ml methanol, which was added to the solution. The solution was concentrated in vacuo to ~75 ml. 350 ml ethyl acetate and 80 ml water were added. The organic layer was washed with 80 ml brine, dried (Na$_2$SO$_4$) and evaporated to dryness, resulting in an orange/brown oil.

Isolated yield: 32.50 g $^1$H-NMR: confirmed the expected structure

To the remaining dark brown oil (3.33 g), 15 ml methanol and 4 ml diethyl ether were added. The mixture was stirred for 2 hours, concentrated in vacuo to ~12 ml and the yellow solution was decanted. To the remaining oil, 10 ml methanol and 2 ml diethyl ether were added. The mixture was stirred for 1 hour, concentrated in vacuo to ~8 ml and the yellow solution was decanted. The collected solutions were evaporated to dryness, resulting in an orange oil.

Isolated yield: 820 mg (desired compound)

Step 2: 2-{1-[({(1R)-1-{3-[(E)-2-(7-chloro-2-quinolinyl)ethenyl]-phenyl}-3-[2-(methoxycarbonyl)phenyl]propyl}sulfanyl)methyl]-cyclopropyl}acetic acid (compound 2)

14.69 g of crude compound (2a) was dissolved in 210 ml tetrahydrofuran. 3.35 g sodium hydroxide dissolved in 420 ml methanol/water (9/1 v/v) was added. The orange/brown solution was stirred at room temperature. Reaction progress was monitored with HPLC. After 40 hours, the reaction mixture was concentrated in vacuo to ~150 ml. 300 ml water was added and the organic solvents were removed in vacuo. 75 ml diethyl ether was added and the mixture was stirred for 10 minutes at room temperature. The water-layer was washed with 75 ml diethyl ether. The combined ether layers were evaporated to dryness, resulting in 3.02 g of an orange/brown oil, mainly containing of starting material and impurities.

300 ml ethyl acetate was added to the water-layer and the pH was adjusted to ~3.5 with 10 M HCl. The organic layer was washed with 100 ml water, followed by wash with 30 ml 5% sodium carbonate solution. The organic layer was washed twice with 25 ml brine, dried (Na$_2$SO$_4$) and evaporated to dryness, resulting in a brown oil/foam.

Isolated yield: ~8.5 g $^1$H-NMR: confirmed the expected structure

Step 3: 2-{1-[({(1R)-{3-[(E)-2-(7-chloro-2-quinolinyl)ethenyl]-phenyl}-3-[2-(1-hydroxy-1-methylethyl)phenyl]propyl}sulfanyl)methyl]-cyclopropyl}acetic acid, (compound (1)

190 mg of the compound (2) was dissolved in 6 ml of dry THF. The reaction mixture was cooled to –30° C. 300 μl methyl lithium complex with lithium bromide (2.2 M solution in diethyl ether) was added dropwise. The reaction was monitored by HPLC; the reaction temperature was kept at –30° C. After 30 minutes, a second addition of 150 μl methyl lithium complex with lithium bromide was made. After 10 minutes at –30° C., HPLC showed the reaction was almost completed. A third addition of 50 μl methyl lithium complex with lithium bromide was made. After 10 minutes, a spatula of ammonium chloride, 20 ml ethyl acetate and 20 ml water were added and the reaction mixture was allowed to warm to room temperature. The organic layer was washed with 2×20 ml brine, dried (Na2SO4) and evaporated to dryness, resulting in a yellow oil. The crude product was purified by column chromatography using silica 60 (Merck) and chloroform as eluens. A yellow compound was isolated.

Isolated yield: ~75 mg $^1$H-NMR: confirmed the expected structure

Each of the patents, articles, and publications mentioned above is incorporated herein by reference in its entirety. The invention having been thus described, it will be obvious to the worker skilled in the art that the same may be varied in many ways without departing from the spirit of the invention and all such modifications are included within the scope of the present invention as set forth in the following claims.

What is claimed is:

1. A process of chemical synthesis, which comprises reacting in the presence of a base a compound of formula (20):

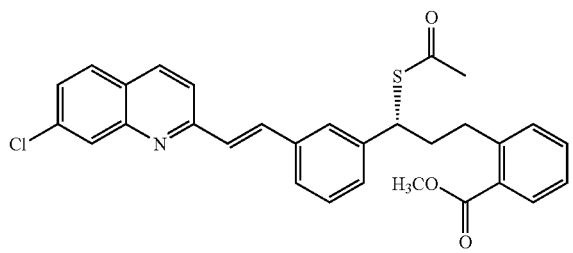

(20)

with a compound of formula (5):

(5)

wherein R is hydrogen or C1-C4 alkyl group, and L is a leaving group selected from a halogen or an alkyl- or arylsulfonyloxy group, to form a compound of formula (2) or (2a):

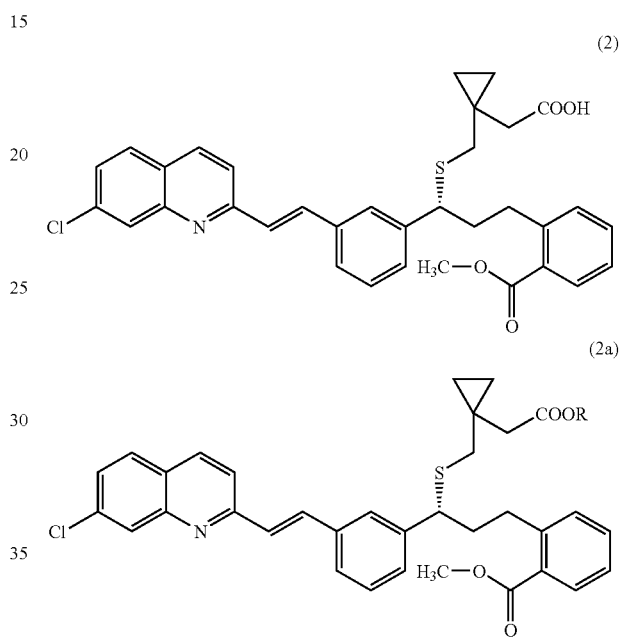

(2)

(2a)

wherein R is a C1-C4 alkyl group.

2. The process according to claim 1, wherein L is a chloro, bromo, mesyloxy, besyloxy or tosyloxy group.

3. The process according to claim 1, wherein said base is lithium hydroxide.

4. The process according to claim 1, which further comprises converting said compound of formula (2) or (2a) to a compound of formula (1):

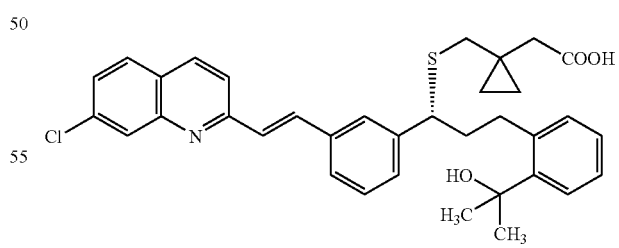

or a salt thereof.

5. The process according to claim 4, wherein said converting step comprises reacting said compound of formula (2) with, methyl lithium to form said compound of formula (1).

6. The process according to claim 5, wherein R is a C1-C4 alkyl group and wherein said converting step further comprises hydrolyzing said compound of formula (2a) to form said compound of formula (2) prior to carrying out said reaction step with said methyl lithium to form said compound of formula (1).

7. The process according to claim 5, wherein said methyl lithium is a complex of methyl lithium with lithium bromide.

8. The process according to claim 7, wherein said reaction of compound (2) with methyl lithium is carried out in an ether solvent.

9. The process according to claim 8, wherein said ether solvent is tetrahydrofuran, diethyl ether or a combination thereof.

10. The process according to claim 1, which further comprises reacting a compound of formula (19)

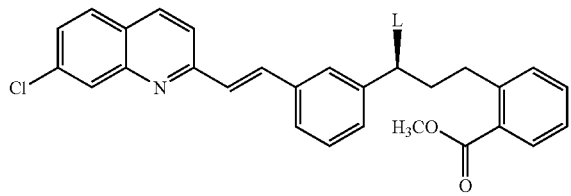

(19)

wherein L is a C1-C4 alkylsulfonyloxy group, with a thioacetic acid or a salt thereof to yield said compound of formula (20).

11. The process according to claim 10, wherein L is a methylsulfonyloxy group and said thioacetic acid or salt thereof is selected from sodium thioacetate and potassium thioacetate.

12. A process for making montelukast, which comprises reactively contacting a compound of formula (2)

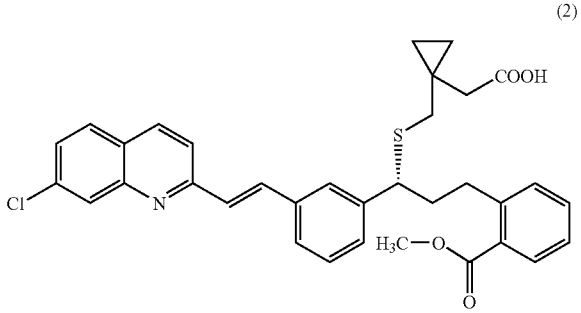

(2)

with a complex of methyl lithium and lithium bromide in an ether solvent to form montelukast of formula (1)

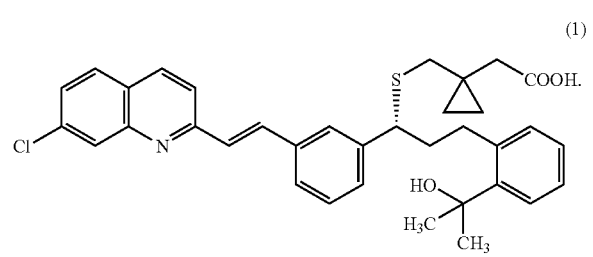

(1)

13. The process according to claim 12, wherein the temperature during said reactive contacting is within the range of −40° C. to −10° C.

14. The process according to claim 13, wherein said ether solvent is tetrahydrofuran, diethyl ether or a combination thereof.

15. A process of forming montelukast, which comprises:
(a) reacting in the presence of a base a compound of formula (20):

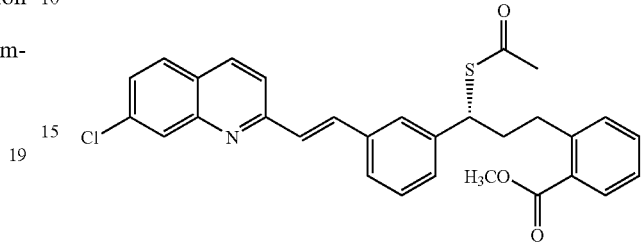

(20)

with a compound of formula (5):

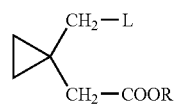

(5)

wherein R is C1-C4 alkyl group, and L is a leaving group selected from a halogen or an alkyl- or aryl-sulfonyloxy group, to form a compound of formula (2a):

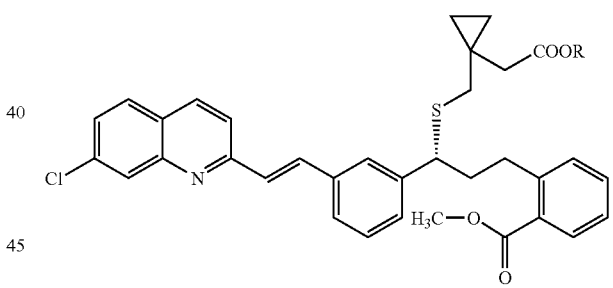

(2a)

wherein R is a C1-C4 alkyl group;
(b) hydrolyzing said compound of formula (2a) to form a compound of formula (2);

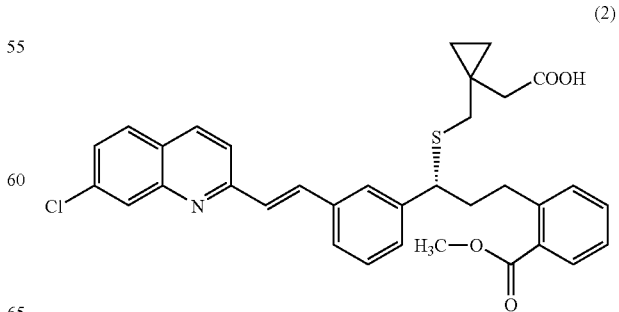

(2)

and (c) reacting said compound of formula (2) with a complex of methyl lithium and lithium bromide in an ether solvent to form montelukast of formula (1)

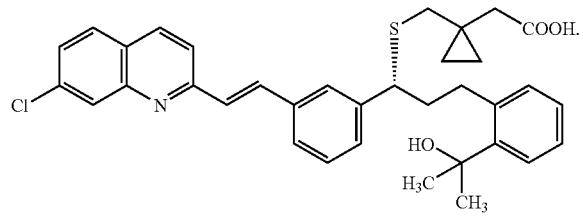

(1)

16. The process according to claim 15, wherein L is a chloro, bromo, mesyloxy, besyloxy or tosyloxy group.

17. The process according to claim 16, wherein said base is lithium hydroxide, R is a methyl or ethyl group, and said ether solvent is tetrahydrofuran, diethyl ether or a combination thereof.

18. The process according to claim 15, wherein said hydrolyzing step (b) uses an alkaline hydrolysis.

19. The process according to claim 15, which further comprises forming a salt of said montelukast of formula (1).

* * * * *